(12) United States Patent
Krumme et al.

(10) Patent No.: US 7,037,526 B1
(45) Date of Patent: May 2, 2006

(54) FILM PREPARATION FOR BIPHASIC RELEASE OF PHARMACOLOGICALLY ACTIVE OR OTHER SUBSTANCES

(75) Inventors: Markus Krumme, Neuwied (DE); Karin Ludwig, Datzeroth (DE)

(73) Assignee: LTS Lohmann Therapie-Syteme AG, Andernach (DE)

( * ) Notice: Subject to any disclaimer, the term of this patent is extended or adjusted under 35 U.S.C. 154(b) by 304 days.

(21) Appl. No.: 10/129,837

(22) PCT Filed: Nov. 3, 2000

(86) PCT No.: PCT/EP00/10861

§ 371 (c)(1),
(2), (4) Date: Jul. 10, 2002

(87) PCT Pub. No.: WO01/35934

PCT Pub. Date: May 25, 2001

(30) Foreign Application Priority Data

Nov. 12, 1999 (DE) .............................. 199 54 421

(51) Int. Cl.
*A61K 9/14* (2006.01)

(52) U.S. Cl. ...................................................... 424/484

(58) Field of Classification Search ................ 424/472, 424/484
See application file for complete search history.

(56) References Cited

U.S. PATENT DOCUMENTS

| 4,765,983 A | 8/1988 | Takayanagi et al. |
| 5,085,865 A | 2/1992 | Nayak |
| 5,393,528 A * | 2/1995 | Staab ......................... 424/436 |
| 5,681,583 A | 10/1997 | Conte et al. |
| 6,294,200 B1 * | 9/2001 | Conte et al. ................. 424/472 |

FOREIGN PATENT DOCUMENTS

WO    WO 96/41617    12/1996

* cited by examiner

*Primary Examiner*—Thurman K. Page
*Assistant Examiner*—Sharon Howard
(74) *Attorney, Agent, or Firm*—Birch, Stewart, Kolasch & Birch, LLP

(57) ABSTRACT

A polymer-based preparation in film form for biphasic release of substances present therein to liquid surroundings, is characterized in that the preparation comprises at least two polymer matrix layers which differ in terms of their construction from polymers, with release taking place rapidly from one of the layers, and release taking place slowly from at least one other layer.

6 Claims, 1 Drawing Sheet

FILM PREPARATION FOR BIPHASIC RELEASE OF PHARMACOLOGICALLY ACTIVE OR OTHER SUBSTANCES

This application is the national phase under 35 U.S.C. § 371 of PCT International Application No. PCT/EP00/10861 which has an International filing date of Nov. 3, 2000, which designated the United States of America.

BACKGROUND OF THE INVENTION

1. Field of the Invention

The invention relates to a preparation in film form which makes biphasic release of substances contained therein to liquid surroundings possible. The invention also includes a process for the production of such preparations, and the use thereof for the release of substances, in particular of drugs, to body fluids in the human or animal body.

2. Description of the Related Art

Applications based on targeted delivery or release of active ingredients or constituents to the surrounding medium depend, in certain cases—for example on administration of medicines from depot pharmaceutical forms—on a high initial dose being released at the start, followed by a lower subsequent or maintenance dose which is, however, constant over a certain period. This is intended to have the effect of very quickly building up a high level of active ingredient in the body fluids, which can then be kept at a desired level by constant administration of the maintenance dose.

In order to achieve rapid release, a preparation or formulation for example of a drug must be designed so that it has a large surface area in relation to the volume. This means that the diffusion pathways are as short as possible, and release of the active ingredient can take place in a very short time. In addition, such a release system ought to be as compact as possible in order to ensure sufficient strength and ease of handling.

A dosage form in film form which contains active ingredients in dissolved, emulsified or suspended form makes it possible, because of the small layer thickness and the correspondingly short diffusion pathways, for release times to be extremely short and thus for delivery of initial doses to be rapid.

The release of the active ingredient can take place either by the latter diffusing out of the matrix in film form, or by the film layer being dissolved or decomposed and the active ingredient thus entering the surroundings.

Active ingredient-containing films whose matrix is based on hydrophilic polymers are already known. These dosage forms in film form may also contain other constituents or auxiliaries to adjust the physicochemical parameters of the film, and the taste or the chemical stability. Films of this type are generally produced by coating an active ingredient- and auxiliary-containing solution of a hydrophilic polymer onto an inert processing sheet. The solvent is then removed by drying, and the active ingredient-containing matrix remains behind as film.

As described, it is also possible with only single-phase dosage forms to achieve rapid release of active ingredient, although in this case delivery of the initial dose is usually followed by an unwanted rapid decline in the effect. There is moreover the risk of overdosage or—in the case of active ingredients which are characterized by an increased concentration-dependent elimination—a wasted dose scenario.

SUMMARY OF THE INVENTION

The present invention is based on the object of avoiding the disadvantages occurring in connection with the use of single-phase dose forms. The object was in particular to provide a system in film form which makes two-phase release of constituents to a liquid medium possible, specifically in such a way that firstly a high initial dose of a substance is delivered to the surroundings, followed by another substance with a slower rate of release.

Specifically, a system of this type ought to make possible the release of drugs in or on the human or animal body. In addition to the desired release characteristics, a system of this type must also have adequate mechanical stability in order to make easy handling possible. The object was further to indicate a production process which is as simple and cost-effective as possible and can be adapted to various modifications.

This object is surprisingly achieved with a polymer-based preparation in film form, for the biphasic release of substances to liquid surroundings, where the preparation has at least two polymer matrix layers differing in their polymeric structure to allow different release rates from different layers. Other embodiments of the invention set forth further useful modifications of the invention.

DETAILED DESCRIPTION

Figure 1:
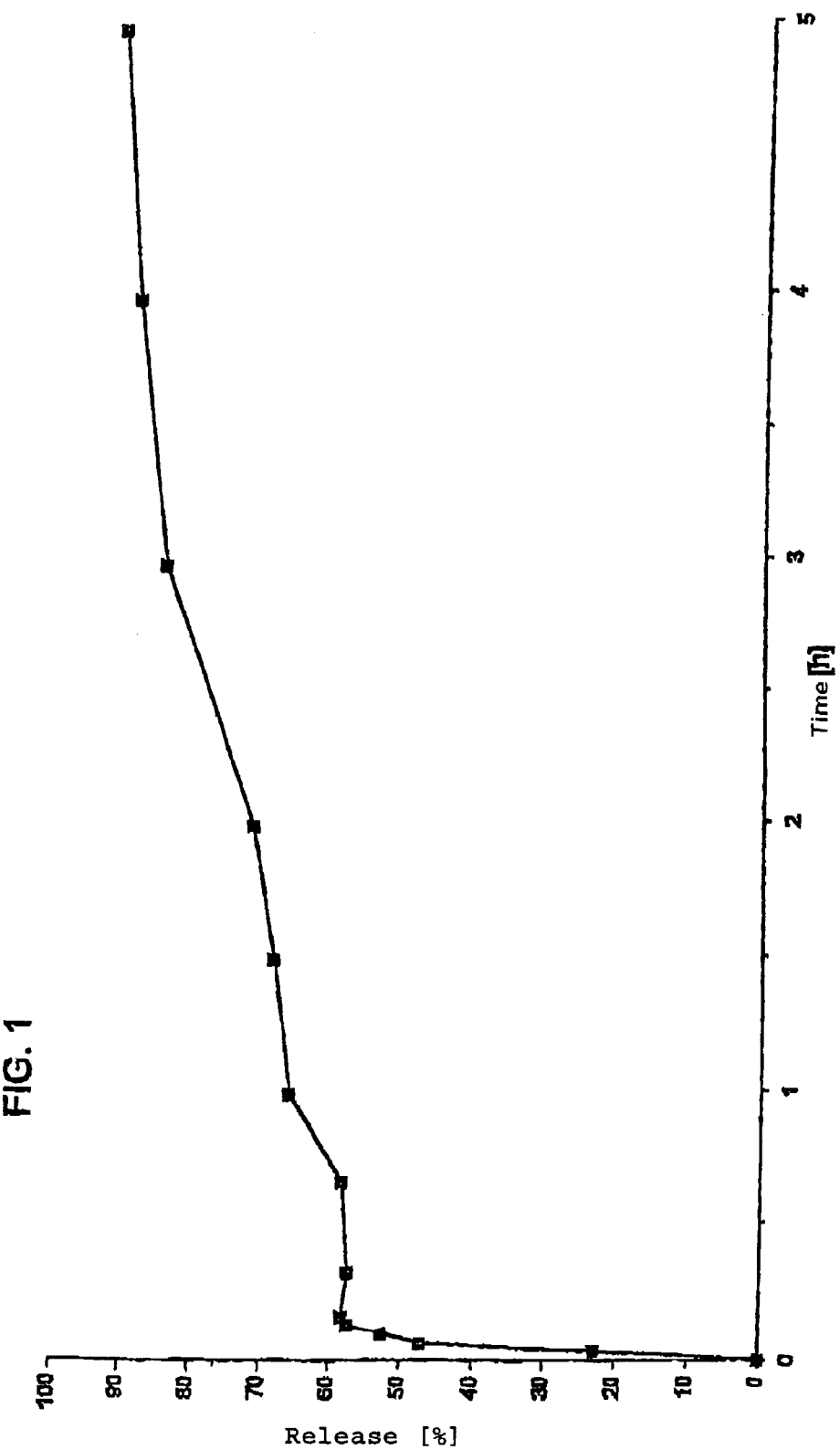
FIG. 1 shows the release of caffeine in water from preparations in film form ("wafers") according to the invention.

The preparations in film form according to the invention are characterized in that they comprise at least two polymer matrix layers which differ in terms of their construction from polymers. This difference in the polymer content has the effect that the release of an active ingredient or of another substance takes place rapidly from one of the layers, and the release takes place slowly from at least one other layer.

The different rates of release in the different film layers are preferably achieved by the matrix of the rapidly releasing layer being composed of hydrophilic polymers or polymers with high solubility in water, or of polymer mixtures with these properties, and by the matrix of the slowly releasing layer(s) being composed of less hydrophilic polymers or polymer mixtures which are less soluble or insoluble in water. This results in the first layer mentioned dissolving rapidly in the manner of a flash release formulation in aqueous surroundings.

By contrast, the slowly releasing layer is, by reason of its specific polymer composition, relatively inert toward aqueous systems and is, as a consequence, only slowly dissolved. Thus, despite its layer thickness likewise being small, it reaches only low release rates. A system with biphasic release characteristics is made possible in this way and can be achieved with small layer thicknesses and therefore has advantages for example in production and handling.

In terms of the rates of release which can be achieved, particularly suitable modifications of the invention are those in which the rate of dissolution of the rapidly releasing layer is adjusted so that an area of at least 10 $cm^2$ of this layer is dissolved in physiological fluids (or in artificial simulations thereof) in less than 15 min, preferably in less than 5 min, particularly preferably in less than 1 min.

Further particularly suitable modifications of the invention are those in which the rate of dissolution of the slowly releasing layer is adjusted so that at least 15 min, preferably at least 60 min, particularly preferably at least 120 min, are required for the dissolution of an area not exceeding 10 cm$^2$ of this layer in physiological fluids (or artificial simulations thereof).

Particularly suitable polymer ingredients of the rapidly releasing layer are polymers or polymer mixtures which are selected from the group which comprises cellulose ethers, polyvinyl alcohol, polyvinyl acetate, polyvinylpyrrolidone, copolymers of the aforementioned polymers, and gelatin, alginates and other natural or partially synthetic polymers. It is also possible to use various other polymers of synthetic, partially synthetic and natural origin which are known to the skilled person.

Particularly preferred preparations in film form are those in which the matrix of the rapidly releasing layer is composed of polyvinyl alcohol or of polyvinyl alcohol-containing polymer mixtures.

In another preferred embodiment, the matrix of the rapidly releasing layer is composed of cellulose ethers, preferably hydroxypropylmethylcellulose, or of mixtures of cellulose ethers.

Polymers preferably used to construct the matrix of the slowly releasing layer(s) are those selected from the group which comprises cellulose ethers, preferably ethylcellulose, and polyvinyl alcohol, polyurethane, polymethacrylates, poly(methyl methacrylates) and derivatives and copolymers of the aforementioned polymers.

The low solubility or insolubility of the polymer film in aqueous medium, or else its water-resistant constitution, results in delivery of active ingredient taking place only slowly by means of diffusion with—when the formulation is suitable—a low diffusion coefficient. This brings about slow delivery of active ingredient.

In order to reduce the solubility or the rate of release of the slowly releasing layer(s) it is possible to subject the polymer layer to a heat treatment. Thus, for example, a highly hydrolyzed polyvinyl alcohol can be employed as basic polymer for the insoluble, slowly releasing layer if this polymer is made insoluble by heat treatment.

It is additionally possible to delay release of active ingredient by other pharmaceutical technology measures, for example by increasing the size of the active ingredient particles, by coating the active ingredient particles or by microencapsulation. Methods of this type can also be used to delay release of the constituents without pharmacological activity.

The preparations in film form according to the invention preferably have a thickness in the range between 5 and 500 µm, particularly preferably in the range between 10 and 100 µm. The active ingredient(s) present in the film polymer matrix are distributed in the form of a true solution (molecular dispersion), a colloidal solution, an emulsion or a suspension in the at least two layers.

It is additionally possible for auxiliaries or additives which are able, for example, to increase the stability of the preparation, to modulate the rate of release, or to improve the absorption or permeation of the active ingredient in the human or animal body, to be present. The auxiliaries or additives include, inter alia, disintegration promoters, plasticizers, wetting agents, structuring agents and texture modifiers.

Preferred embodiments of the preparations in film form according to the invention contain in at least one of the layers a pharmacologically active ingredient or a plurality of such active ingredients. The second layer or—in the case of a multilayer structure—the further layers may contain either an odorizer, flavoring, sweetener or other constituent, or likewise a drug. The latter may also be identical to the drug in the first layer. Combinations of different drugs or other constituents may also prove to be worthwhile.

Besides the possibility of delivering an active ingredient (or a plurality of active ingredients) initially rapidly and then slowly in two consecutive phases, the spatial separation in different active ingredient-containing compartments in the form of a plurality of layers is also advantageous for other reasons. Thus, it is possible to combine two or more active ingredients which are mutually incompatible in separate layers. A further possibility is for the active ingredient or active ingredients also to be spatially separated from odorizers, sweeteners etc. which are additionally present. It is possible in this way to avoid some incompatibilities, and new types of combinations of active ingredients with one another and with other constituents which can be administered together in a multilayer preparation in film form according to the invention are possible.

The preparations in film form according to the invention are in principle always suitable when one or more substances are to be delivered to liquid surroundings in a biphasic scheme characterized by initially rapid and subsequently slow release. The systems according to the invention are preferably employed in order to deliver constituents, in particular pharmacologically active substances, to body fluids. For this purpose the preparations in film form are administered in body orifices, body cavities or the interior of the body of human or animal organisms. The influence of the surrounding body fluids (for example saliva, gastric fluid) then brings about the predetermined dissolution at different rates of the individual layers, resulting in the rapid or slow release of the active pharmaceutical ingredients or other constituents.

The preparations in film form are, of course, also suitable for delivering substances to synthetic simulations of body fluids. Because of their ability to deliver drugs with biphasic release characteristics to body fluids, the film preparations according to the invention can advantageously be employed for medical therapy or prophylaxis of a wide variety of pathological manifestations.

It is possible to employ for producing the compositions in film form with biphasic release a variety of process variants proposed according to the invention. The production procedure is preferably such that there is initial production of a film-forming solution which contains the polymers or polymer mixtures suitable for producing rapidly dissolving and releasing layers, and to which the active ingredients or other constituents to be released are added. It is likewise possible—where necessary—to add further auxiliaries or additives.

The solution obtained in this way, which must have a viscosity suitable for further processing, is then coated by knife or roller application or spraying processes onto an inert substrate and dried, which removes the solvent and forms a film (the layer produced first in each case is also referred to hereinafter as "initial film"). The suitable inert substrates are known to the skilled worker and may, for example, be in the form of processing sheets or metal strips. Both continuous coating processes and batchwise processes are possible, coating being possible in principle on any inert surfaces.

For the slowly releasing layer, a solution which contains a suitable polymer or polymer mixture and active ingredients and/or constituents and, where appropriate, auxiliaries and additives is produced in an analogous manner. Selection of the solvents must take account of the fact that they must not attack the initial layer. The solution is applied by one of the aforementioned coating processes or else by printing onto the prepared initial film and is then dried, resulting in a film composite or laminate. It is also possible in a corresponding way to add further slowly releasing layers. It is likewise possible to prepare the second or following layer on an inert carrier and then to laminate onto the initial layer.

In a particularly advantageous variant of the production process, the sequence of the process steps is altered so that initially the slightly soluble or slowly releasing polymer solution is applied as "initial layer" to an inert carrier. After drying of this layer the readily soluble or rapidly releasing film layer is applied thereto. This procedure makes it possible, for example, to employ a highly hydrolyzed polyvinyl alcohol as basic polymer for the slightly soluble or insoluble layer, which polymer is rendered insoluble by heat treatment. The second (water-soluble, rapidly releasing) film can be formulated for example by partially hydrolyzed polyvinyl alcohol, which is layered onto the heat-treated (initial) film.

A further variant of the production process according to the invention provides for producing the initial film from a polymer melt which is coated by knife or roller application, spraying or extrusion processes onto an inert substrate and is then cooled and/or dried. The second or the further layers are then applied to this initial layer from solutions as described above, using solvents which do not attack or dissolve the initial layer.

The invention is explained in detail by the following examples

EXAMPLES

Example 1

Partially hydrolyzed polyvinyl alcohol of low viscosity (Mowiol® 8-88, supplied by Clariant) is dissolved in hot water. A viscous composition is produced therefrom by adding suitable auxiliaries such as plasticizers, disintegration promoters, wetting agents and similar additives known to the skilled worker, and the active ingredients, and is coated onto an inert substrate.

Drying results in a film ("initial film") which is easy to handle and is readily soluble in water and contains
28.6% by weight of Mowiol® 8-88,
7.9% by weight of titanium dioxide,
37.2% by weight of silicon dioxide,
11.5% by weight of polyethylene glycol 400,
4.6% by weight of polyethylene glycol 4000, and
10.2% by weight of sorbitol.

A second composition based on ethylcellulose is produced in a corresponding manner and is dissolved in ethanol and likewise contains active ingredients and suitable auxiliaries similar to the first layer, namely
about 57% by weight of ethylcellulose,
about 5% by weight of Lanette O (wax-like ointment base containing cetylstearyl alcohol, in a mixture of 1-hexadecanol and 1-octadecanol)
about 30% by weight of silicon dioxide and
about 8% by weight of titanium dioxide.

The initial layer (Mowiol® 8-88) is insoluble in ethanol and therefore shows inert behavior toward the second coating composition, which can be applied to the Mowiol film. The composite is dried to result in a film formulation with biphasic release (=preparation in film form).

With preparations in film form (also called "wafers") with a size of 15×15 mm it is possible in this case to achieve, by suitable formulations, in vitro release times which—as intended—are in the region of less than 60 s for the rapidly dissolving layer and in the region of a few hours for the slowly dissolving layer.

Example 2

Formulas for Biphasic Systems

Polymer Film with Biphasic Release Containing Caffeine Citrate as Active Ingredient.

A system with biphasic release (preparation in film form) with caffeine as active ingredient was produced by the production process indicated in Example 1. The first coating composition and the second coating composition had the following compositions in this case:

Coating Composition for the First Layer (Initial Film):
"BMX 0001": solids content 50.41% by weight
7.14% by weight of titanium dioxide
25.88% by weight of polyvinyl alcohol
9.52% by weight of caffeine citrate
4.13% by weight of polyethylene glycol 4000
10.35% by weight of polyethylene glycol 400
9.32% by weight of sorbitol
33.65% by weight of silicon dioxide
water as solvent.

Coating Composition for the Second Layer:
"BMX 0002": solids content 22.49% by weight
86.16% by weight of ethylcellulose
4.31% by weight of cetylstearyl alcohol
9.53% by weight of caffeine citrate
ethanol as solvent These coating compositions were used to produce preparations in film form ("wafers") as described in Example 1, and the release of caffeine in water from these preparations in film form was investigated. The test results are presented in the graph in FIG. 1.

FIG. 1 shows the release of caffeine in water from preparations in film form ("wafers") according to the invention. The release plot shown in FIG. 1 reveals very clearly the two-phase delivery characteristics: a rapid release ("initial burst") within about 10 minutes and a slow but continuous and controlled release over the remaining period (in the specific case: 5 hours).

The indicated releases were measured by "paddle over disc" and "rotary basket" methods. The individual points in the release plot are averages of measurements using different measurement methods.

The invention claimed is:

1. A process for the production of a polymer-based preparation in film form, for biphasic release of substances contained therein to liquid surroundings, the preparation comprising at least two polymer matrix layers which differ in terms of their construction from polymers, with release taking place rapidly from one of the layers, and release taking place slowly from at least one other layer, said matrix of the rapidly releasing layer comprising a polyvinyl alcohol or a polyvinyl alcohol-containing polymer mixture, and said matrix of the slowly releasing layer(s) comprising at least one polymer selected from the group consisting of cellulose ethers, polyurethane, polymethacrylates, poly(methyl methacrylates) and derivatives or copolymers thereof, said process comprising the following steps:
a) providing a polymer solution suitable for the rapidly releasing layer, comprising the substances to be released;
b) coating of the polymer solution onto an inert substrate by knife or roller application or spraying processes and subsequent drying to form the rapidly releasing film layer;
c) providing a polymer solution suitable for the slowly releasing layer, comprising the substances to be released; and
d) coating of this solution onto the rapidly releasing film layer by knife or roller application or spraying processes or printing and subsequent drying to form the slowly releasing film layer.

2. A process for the production of a polymer-based preparation in film form, for biphasic release of substances contained therein to liquid surroundings, the preparation comprising at least two polymer matrix layers which differ in terms of their construction from polymers, with release taking place rapidly from one of the layers, and release taking place slowly from at least one other layer, said matrix of the rapidly releasing layer comprising a polyvinyl alcohol or a polyvinyl alcohol-containing polymer mixture, and said matrix of the slowly releasing layer(s) comprising at least one polymer selected from the group consisting of cellulose ethers, polyurethane, polymethacrylates, poly(methyl methacrylates) and derivatives or copolymers thereof, said process comprising the following steps:
a) providing a polymer solution suitable for the slowly releasing layer, comprising the substances to be released;
b) coating of the polymer solution onto an inert substrate by knife or roller application or spraying processes and subsequent drying to form the rapidly releasing film layer;
c) providing a polymer solution suitable for the rapidly releasing layer, comprising the substances to be released; and
d) coating of this solution onto the slowly releasing film layer by knife or roller application or spraying processes or printing and subsequent drying to form the slowly releasing film layer.

3. The process according to claim 1, wherein production of the first film layer starts from a polymer melt which is applied by knife or roller application, spraying or extrusion processes to an inert substrate and is then dried and/or cooled, and the further layers are coated from polymer solutions.

4. The process according to claim 1, wherein the release of the substance(s) from the slowly releasing layer(s) is further delayed by increasing the size of the substance particles, by coating or by microencapsulation of the substance or of the active ingredient, or by pharmaceutical technology measures having similar effects.

5. A method for the release of substances or active pharmaceutical ingredients into human or animal body fluids or artificial simulations of such body fluids, which comprises:
applying to a subject in need thereof a polymer-based preparation in film form for biphasic release of substances contained therein to liquid surroundings, the preparation comprising at least two polymer matrix layers which differ in terms of their construction from polymers, with release taking place rapidly from one of the layers, and release taking place slowly from at least one other layer, said matrix of the rapidly releasing layer comprising a polyvinyl alcohol or a polyvinyl alcohol-containing polymer mixture, and said matrix of the slowly releasing layer(s) comprising at least one polymer selected from the group consisting of cellulose ethers, polyurethane, polymethacrylates, poly(methyl methacrylates) and derivatives or copolymers thereof.

6. A method for producing pharmaceutical preparations for medical therapeutic treatment of diseases in humans or animals, which comprises:
incorporating a pharmaceutically active substance into a polymer-based preparation in film form for biphasic release of substances contained therein to liquid surroundings, the preparation comprising at least two polymer matrix layers which differ in terms of their construction from polymers, with release taking place rapidly from one of the layers, and release taking place slowly from at least one other layer, said matrix of the rapidly releasing layer comprising a polyvinyl alcohol or a polyvinyl alcohol-containing polymer mixture, and said matrix of the slowly releasing layer(s) comprising at least one polymer selected from the group consisting of cellulose ethers, polyurethane, polymethacrylates, poly(methyl methacrylates) and derivatives or copolymers thereof.

* * * * *